(12) United States Patent
Parramon et al.

(10) Patent No.: US 10,420,950 B2
(45) Date of Patent: Sep. 24, 2019

(54) IMPLANTABLE PULSE GENERATOR USABLE DURING A TRIAL STIMULATION PHASE AND EXTERNALLY POWERED BY MAGNETIC INDUCTIVE COUPLING

(71) Applicant: Boston Scientific Neuromodulation Corporation, Valencia, CA (US)

(72) Inventors: Jordi Parramon, Valencia, CA (US); Anne Pianca, Valencia, CA (US); Bernard Malinowski, Castaic, CA (US); William G. Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 109 days.

(21) Appl. No.: 15/334,043

(22) Filed: Oct. 25, 2016

(65) Prior Publication Data
US 2017/0151440 A1    Jun. 1, 2017

Related U.S. Application Data

(60) Provisional application No. 62/260,620, filed on Nov. 29, 2015.

(51) Int. Cl.
*A61N 1/37* (2006.01)
*A61N 1/378* (2006.01)
*A61N 1/36* (2006.01)
*A61N 1/372* (2006.01)
*A61N 1/375* (2006.01)

(52) U.S. Cl.
CPC ....... *A61N 1/3787* (2013.01); *A61N 1/36125* (2013.01); *A61N 1/37223* (2013.01); *A61N 1/37241* (2013.01); *A61N 1/36062* (2017.08); *A61N 1/3758* (2013.01)

(58) Field of Classification Search
CPC .............. A61N 1/3787; A61N 1/36125; A61N 1/37223
See application file for complete search history.

(56) References Cited

U.S. PATENT DOCUMENTS 6,516,227 B1    2/2003 Meadows et al.
7,444,181 B2    10/2008 Shi et al.
(Continued)

FOREIGN PATENT DOCUMENTS

WO    2012/138782    10/2012

*Primary Examiner* — Tammie K Marlen
(74) *Attorney, Agent, or Firm* — Lewis & Reese, PLLC

(57) ABSTRACT

An implantable pulse generator (IPG) allowing for trial stimulation in a fully implanted solution is disclosed. At the time the leads are implanted, a micro IPG having lead connection block(s) is also implanted and connected to the leads. To keep the micro IPG suitably small, it preferably does not include a battery, and is instead powered continuously via magnetic induction using a magnetic field produced by an external charger, such as a charging patch. A coil in the micro IPG picks up and rectifies this magnetic field to provide power to stimulating electronics in the IPG. Because of its small size (e.g., ≤10 cm$^3$), implantation of the micro IPG can occur at the same time the leads are implanted in the patient without inconvenience. Should stimulation therapy with the micro IPG prove effective, a larger, permanent IPG can later be implanted and connected to the implanted leads.

20 Claims, 9 Drawing Sheets

(56) References Cited

U.S. PATENT DOCUMENTS

| | | |
|---|---|---|
| 8,335,569 B2 | 12/2012 | Aghassian |
| 8,498,716 B2 | 7/2013 | Chen et al. |
| 8,606,362 B2 | 12/2013 | He et al. |
| 8,620,436 B2 | 12/2013 | Parramon et al. |
| 8,694,120 B2 | 4/2014 | Murtonen |
| 8,768,453 B2 | 7/2014 | Parramon et al. |
| 8,862,235 B1 | 10/2014 | Stover et al. |
| 2012/0221074 A1 | 8/2012 | Funderburk et al. |
| 2012/0283800 A1 | 11/2012 | Perryman et al. |
| 2013/0066400 A1 | 3/2013 | Perryman et al. |
| 2013/0079849 A1 | 3/2013 | Perryman et al. |
| 2013/0123868 A1* | 5/2013 | Barker ............... A61N 1/05 607/2 |
| 2013/0289662 A1* | 10/2013 | Olson ............... A61N 1/3787 607/61 |
| 2013/0310901 A1 | 11/2013 | Perryman et al. |
| 2014/0058480 A1 | 2/2014 | Perryman et al. |
| 2014/0358194 A1 | 12/2014 | Vansickle et al. |
| 2015/0066114 A1 | 3/2015 | Bunyan et al. |
| 2015/0080982 A1 | 3/2015 | Van Funderburk |
| 2015/0251011 A1 | 9/2015 | Ranpura et al. |
| 2015/0360038 A1 | 12/2015 | Zottola et al. |
| 2016/0367822 A1 | 12/2016 | Parramon |
| 2017/0151438 A1 | 6/2017 | Orinski |

\* cited by examiner

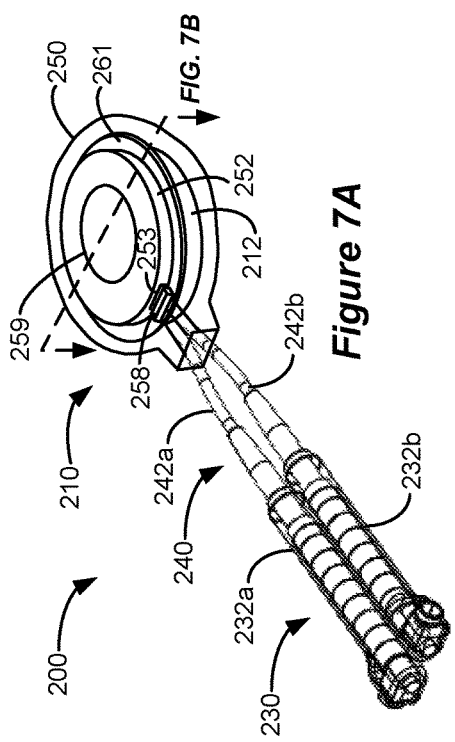
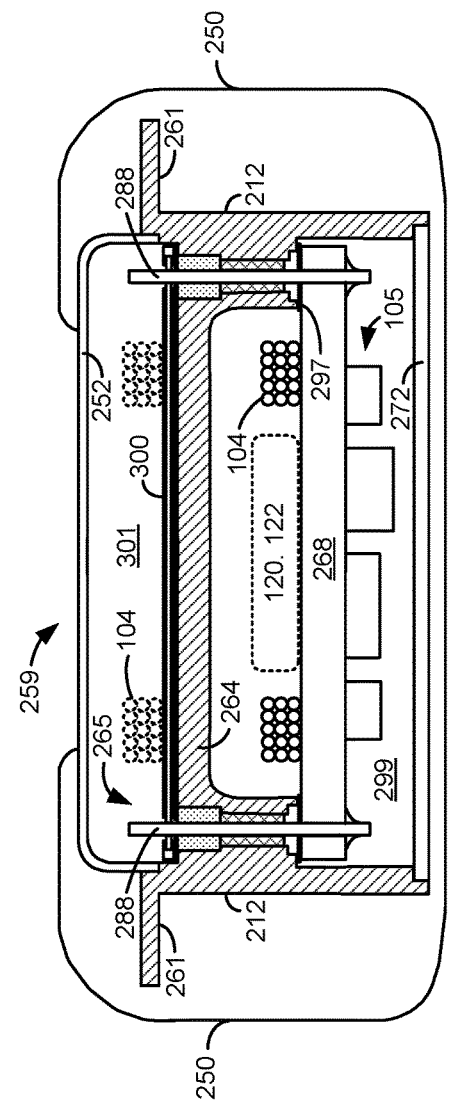

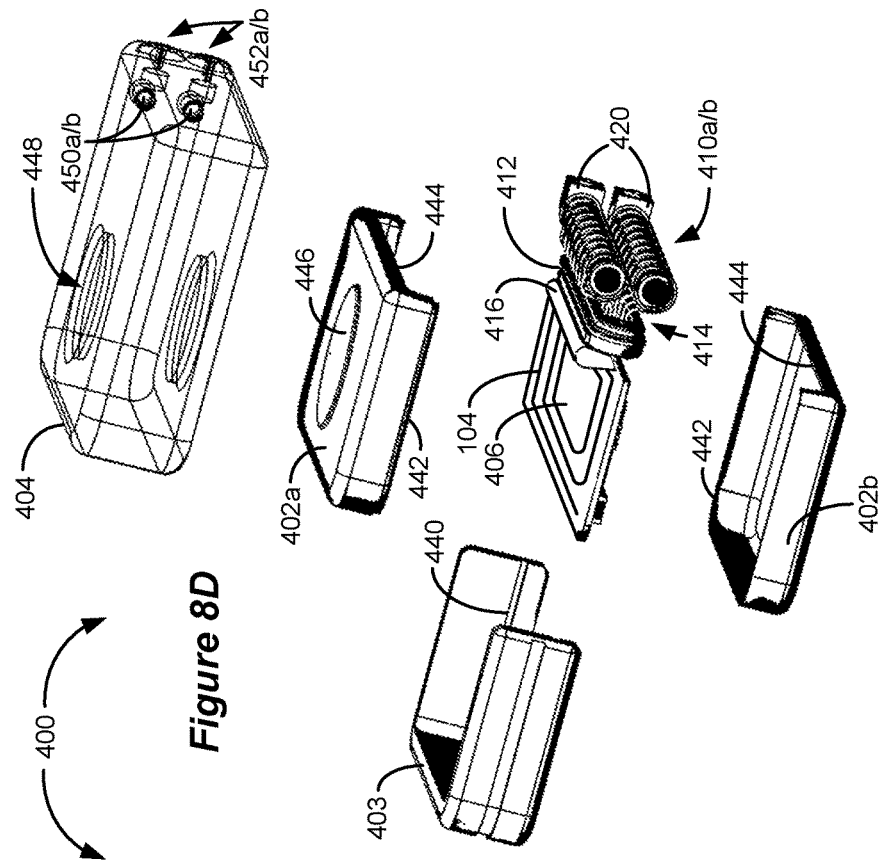
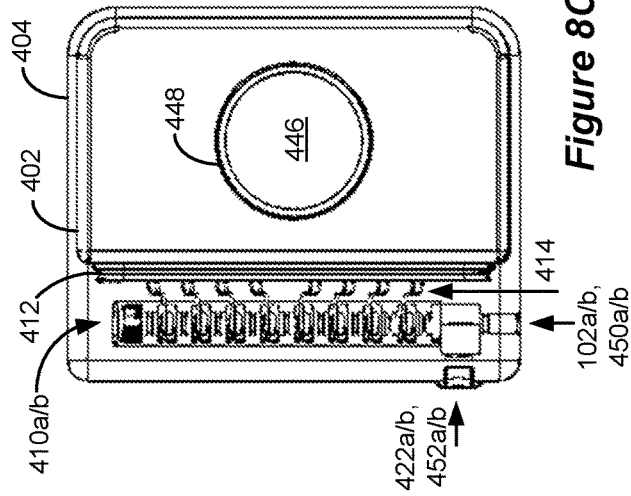
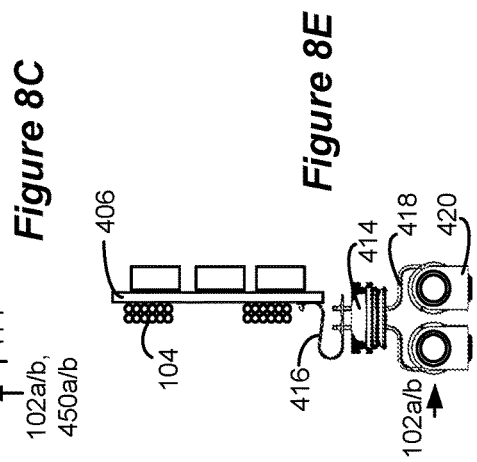

IMPLANTABLE PULSE GENERATOR USABLE DURING A TRIAL STIMULATION PHASE AND EXTERNALLY POWERED BY MAGNETIC INDUCTIVE COUPLING

CROSS-REFERENCE TO RELATED APPLICATIONS

This is a non-provisional application based on U.S. Provisional Patent Application Ser. No. 62/260,620, filed Nov. 29, 2015, to which priority is claimed, and which is incorporated by reference in its entirety.

FIELD OF THE INVENTION

The present application relates to an implantable pulse generator (IPG) system, including an IPG which may be temporary in nature and eventually replaceable by a longer-term traditional IPG.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Pulse Generator (IPG) or in any IPG system.

As shown in FIG. 1, a SCS system includes an Implantable Pulse Generator (IPG) 10, which includes a biocompatible device case 12 formed of titanium for example. The case 12 typically holds the circuitry and battery 14 (FIG. 2) necessary for the IPG 10 to function, which battery 14 may be either rechargeable or primary in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 make contact with the electrode terminals 20, and communicate with the circuitry inside the case 12 via feedthrough pins 26 passing through a hermetic feedthrough 28 to allow such circuitry to provide stimulation to or monitor the various electrodes 16.

In the illustrated embodiment, there are sixteen electrodes 16 split between two leads 18, although the number of leads and electrodes is application specific and therefore can vary. In an SCS application, two electrode leads 18 are typically implanted on the right and left side of the dura within the patient's spinal column. The proximal ends of the leads 18 with the electrode terminals 20 are then tunneled through the patient's flesh to a distant location, such as the buttocks, where the IPG case 12 is implanted, at which point they are coupled to the lead connectors 22.

As shown in FIG. 2, IPG 10 contains a charging coil 30 for wirelessly charging of the IPG's battery 14 using an external charging device 50, assuming that battery 14 is rechargeable battery. If IPG 10 has a non-rechargeable (primary) battery 14, charging coil 30 in the IPG 10 and external charger 50 can be dispensed with. IPG 10 also contains a telemetry coil antenna 32 for wirelessly communicating data with an external controller device 40, also explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16, and may also include telemetry modulation and demodulation circuitry for enabling bidirectional wireless communications at antenna 32; battery charging and protection circuitry coupleable to charging coil 30; DC-blocking capacitors in each of the current paths proceeding to the electrodes 16, etc. Components within the case 12 are integrated via a printed circuit board (PCB) 38.

FIG. 2 further shows the external components referenced above in plan and cross sections that may be used to communicate with the IPG 10. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the microstimulator's battery 14 (FIG. 1) should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a signal external system, such as disclosed in U.S. Pat. Nos. 8,335,569 and 8,498,716.

Implantation of IPG 10 in a patient is normally a multi-step process, as explained with reference to FIG. 3. A first step involves implantation of the distal ends of the lead(s) 18 with the electrodes 16 into the spinal column 60 of the patient through a temporary incision 62 in the patient's tissue 5. The proximal ends of the leads 18 including the electrode terminals 20 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 18 and the ETS 70, ETS extender cables 80 may be used that includes receptacles 82 (similar to the connector blocks 22 (FIG. 1) in the IPG 10) for receiving the electrode terminals 20 of leads 18, and connectors 84 for meeting with ports 72 on the ETS 70, thus allowing the ETS 70 to communicate with each electrode 16 individually. Once connected to the leads 18, the ETS 70 can then be affixed to the patient in a convenient fashion for the duration of the trial stimulation phase, such as by placing the ETS 70 into a belt worn by the patient (not shown).

The ETS 70 essentially mimics operation of the IPG 10 to provide stimulation to the implanted electrodes 16. This allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. Although not shown, the ETS 70 typically contains a battery within its housing along with stimulation and communication circuitry.

The stimulation program executed by the ETS 70 can be provided or adjusted via a wired or wireless link 92 (wireless shown) from a clinician programmer 90. As shown, the clinician programmer 90 comprises a computer-type device, and may communicate wirelessly via link 92 using a communication head or wand 94 wired to the computer. Communication on link 92 may comprise magnetic inductive or short-range RF telemetry schemes as already described, and in this regard the ETS 70 and the clinician's programmer 90 and/or communication head 94 may include antennas compliant with the telemetry means chosen. Clinician programmer 90 may be as described in U.S. Patent Application Publication 2015/0360038. Note that the external controller 40 (FIG. 2) may also communicate with the ETS 70 to allow the patient means for providing or adjusting the ETS 70's stimulation program.

At the end of the trial stimulation phase, a decision is made whether to abandon stimulation therapy, or whether to provide the patient with a permanent IPG 10 such as that shown in FIG. 1. Should it be determined that stimulation therapy is not working for the patient, the leads 18 can be explanted from the patient's spinal column 60 and incision 62 closed in a further surgical procedure.

By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks), with the proximal ends of leads 18 including electrode terminals 20 tunneled through the tissue 5 and coupled to the connection blocks 22 in the IPG's header 24. Thereafter, temporary incision 62 can be closed, and the ETS 70 dispensed with. The result is fully-implanted stimulation therapy solution. If a particular stimulation program(s) had been determined during the trial stimulation phase, it/they can then be programmed into and executed by the IPG 10, and thereafter modified wirelessly using either the external programmer 40 or the clinician programmer 90.

While trial stimulation can be effective, the inventors have concerns with this approach. In particular, stimulation during the trial stimulation phase requires a temporary incision 62 to allow communications between the implanted electrodes 16 and the external ETS 70. While proper bandaging and antibiotics can help mitigate the risk of infection at the incision 62, it is nonetheless unfortunate that the incision must remain open thought the trial period. Because it is not prudent to allow incision 62 to remain open for an extended period of time, the trial stimulation phase is effectively limited in time by the need to close this incision (typically two weeks or less). In other words, even though it may be desirable in some cases to run trial stimulation for longer periods, the need to close the incision 62 may cut such experimentation short, thus forcing a premature decision whether to proceed with implantation of the IPG 10.

A further concern in the inventors' opinion is the fact that implantation of the IPG 10 is essentially a two-step procedure, requiring implantation of the leads 18, followed just weeks later by permanent implantation of the IPG 10. This is difficult on the patient, who must undergo two surgical procedures in a short period of time.

These problems have caused the inventors to think of new solutions, and specifically fully-implanted solutions in which stimulation therapy can be tried at least temporarily, as disclosed herein.

BRIEF DESCRIPTION OF THE DRAWINGS

FIGS. 7A-7E show a second example of a micro IPG, in accordance with an example of the invention.

FIGS. 8A-8E show a third example of a micro IPG, in accordance with an example of the invention.

DETAILED DESCRIPTION OF THE INVENTION

Figure 3:
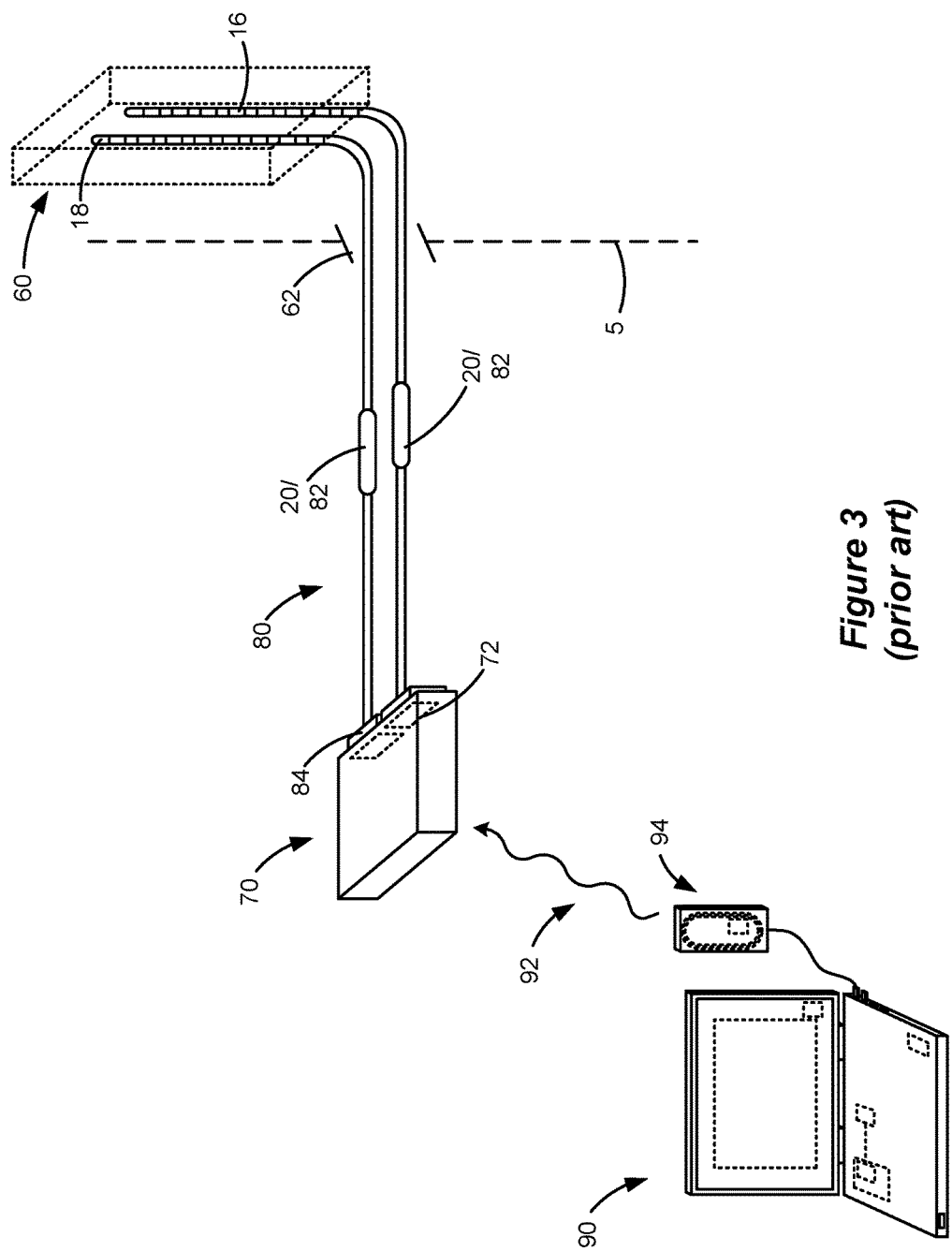
FIG. 3 shows use of trial stimulation preceding implantation of the IPG, including implanted leads/electrodes communicating with an External Trial Stimulator (ETS), in accordance with the prior art.

The inventors realize that traditional external trial stimulation techniques as described earlier (FIG. 3) are driven at least in part by the size of the IPG 10. Even though manufacturers labor to make IPGs such as 10 as small as possible (e.g., between 10-40 cm³ in volume at the current time), such IPGs are still significant in size, particularly because the battery 14 (whether rechargeable or primary) is relatively large. It is therefore generally desired by patients and clinician alike that the IPG 10 only be implanted once stimulation therapy effectiveness has been verified during the ETS trial period. But as mentioned, the extra surgical step required in permanent IPG implantation is inconvenient, particularly because it must occur relatively soon after implantation of the leads (e.g., within two weeks). Nonetheless, such quick implantation of the permanent IPG must occur due to the limited time that the incision 62 is prudently left open.

Accordingly, the inventors disclose an implantable medical device system which allows for trial stimulation to occur in a fully implanted solution not involving an open incision. At the time the leads are implanted, a "micro" IPG having lead connection block(s) is also implanted and connected at least temporarily to the leads. In this fully-implanted solution, the micro IPG can provide trial stimulation over a longer period (e.g., greater than two weeks) and perhaps beyond a trial period. To keep the micro IPG suitably small, it preferably does not include an internal battery, although it may also include a very small capacity battery or capacitor acting as an internal power source to provide the micro IPG power in limited circumstances. Preferably, the micro IPG is provided continuous power from a magnetic field produced by an external charger device, which may take the form of a charging patch. A coil in the micro IPG picks up and rectifies this magnetic field to provide power to stimulating electronics in the IPG, and also to recharge the small battery or capacitor if present.

Because of its small size (less than 10 cm³, and preferably less than or equal to 5 cm³), implantation of the micro IPG can occur at the same time the leads are implanted in the patient without additional surgical inconvenience and risk. Should stimulation therapy as provided by the micro IPG prove unsuccessful, the leads and the micro IPG may be explanted at a convenient later time not dictated by considerations of an open incision, which again is not present in the disclosed technique. Should stimulation therapy prove effective, the micro IPG can continue to be used by the patient for stimulation during an extended trial period or even beyond, although such stimulation will require use of the continuous external charger. Should it eventually be decided that stimulation therapy is effective enough to warrant implant of a traditional, larger, permanent IPG such as 10 discussed earlier, such implantation can occur at a convenient time for the patient and clinician. At such time, the leads can be disconnected from the connector block(s) of the micro IPG, the micro IPG explanted, the permanent IPG implanted in its place (in a larger surgical pocket), and the leads then connected to the connector blocks on the permanent IPG.

Figure 2:
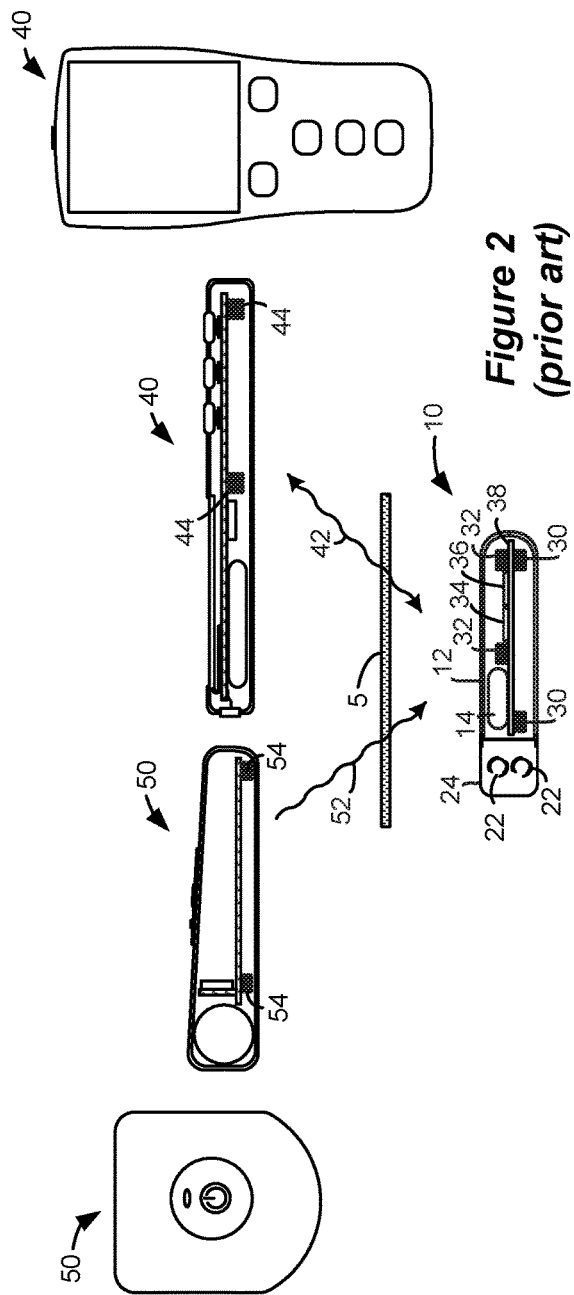
FIG. 2 shows a cross section of the IPG of FIG. 1 as implanted in a patient, as well as external devices that support the IPG, including an external charger and external controller, in accordance with the prior art.

Eventual replacement of the micro IPG with the permanent IPG (while not strictly required) can convenience the patient, who will no longer need to ensure that power is continuously applied to his implant. The permanent IPG may include a rechargeable battery, which need be charged only occasionally by a traditional external charger (e.g., 50, FIG. 2). Alternatively, the permanent IPG may include a primary battery that does not require charging at all. See, e.g., U.S. Patent Application Publication 2015/0066114.

Figure 4:
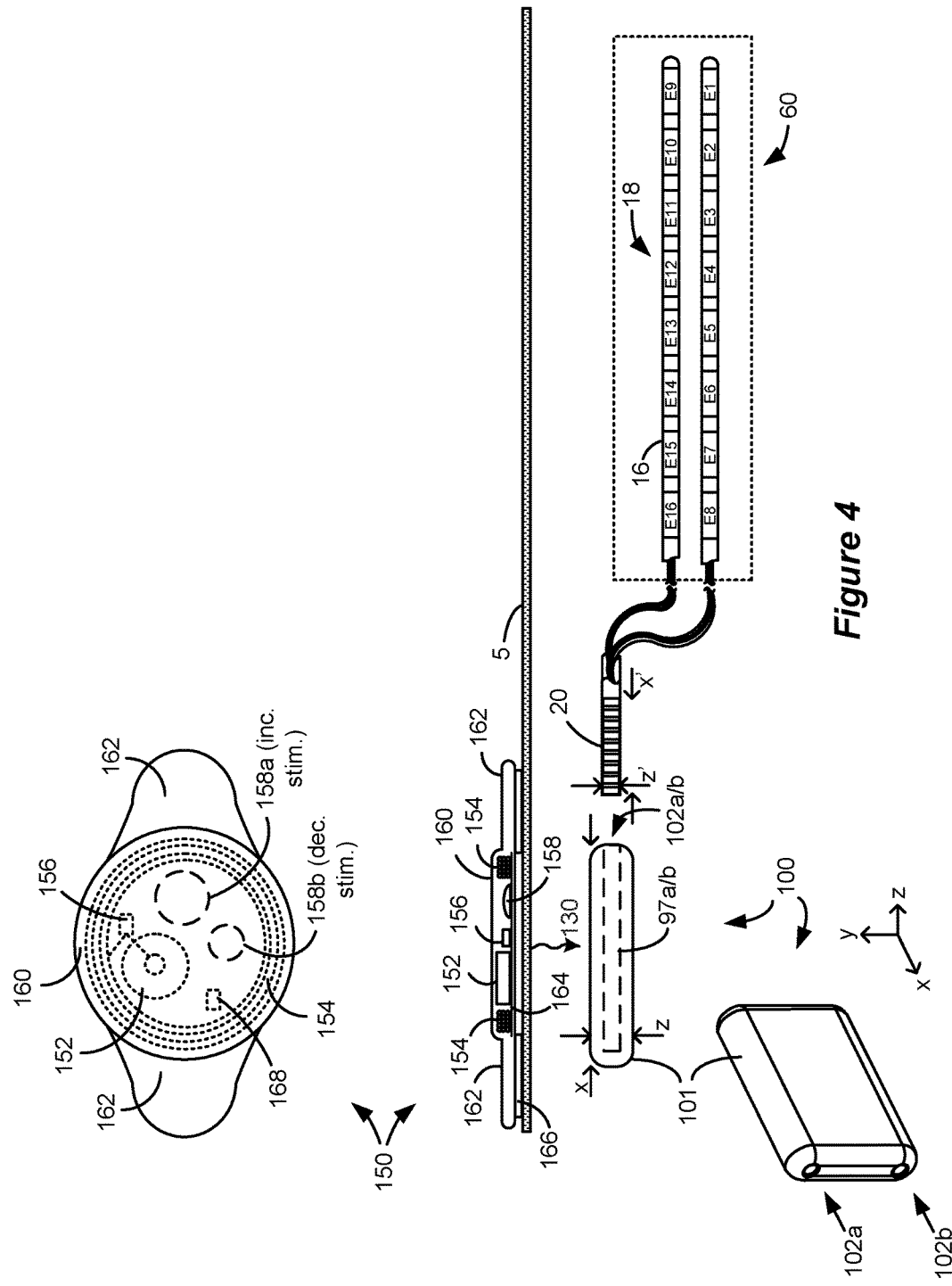
FIG. 4 shows use of a fully implanted micro IPG that can be used during trial stimulation, and which is continuously powered by magnetic induction by a charging patch, in accordance with an example of the invention.

A first example of a micro IPG 100 as described above and as implanted in a patient's tissue 5 is shown in FIG. 4. As shown, the micro IPG 100 includes a rectangularly-shaped housing 101 with edges that are preferably curved to render an overall shape that has no sharp edges and is thus comfortable for the patient. Housing 101 includes two openings 102a and 102b meeting with two connector blocks 97a/b inside of the housing 101 that are configured to receive the electrode terminals 20 of the proximal ends of the implanted leads 18. Internal connector blocks 97a/b run parallel to the x dimension. The two openings 102a and 102b and their connector blocks 97a/b in this example are separated along the y dimension, with internal electronics between them in the housing 101, as shown later with respect to FIG. 6. Note that to accommodate the electrode terminals 20, dimension x of the housing 101 is at least as long as the length x' of the electrode terminals 20. Dimension z of the housing 101 is at least as great as the diameter z' of the electrode terminals 20, and preferably larger to accommodate radii of curvature of the housing 101, as well as electronics within the housing, to be described later. Dimension y is also essentially dictated by room required for internal electronics and a secondary charging/telemetry coil 104, as explained further below. In all, and accounting for lost volume resulting from the housing 101's curved edges, the housing 101 may have a volume of less than 5 cm³, but this could be larger or smaller depending on the application at hand. As discussed above, such small size of the micro IPG 100 is facilitated by its lack of an internal power source such as a battery or capacitor, although very small power sources could also be included.

Figure 5:
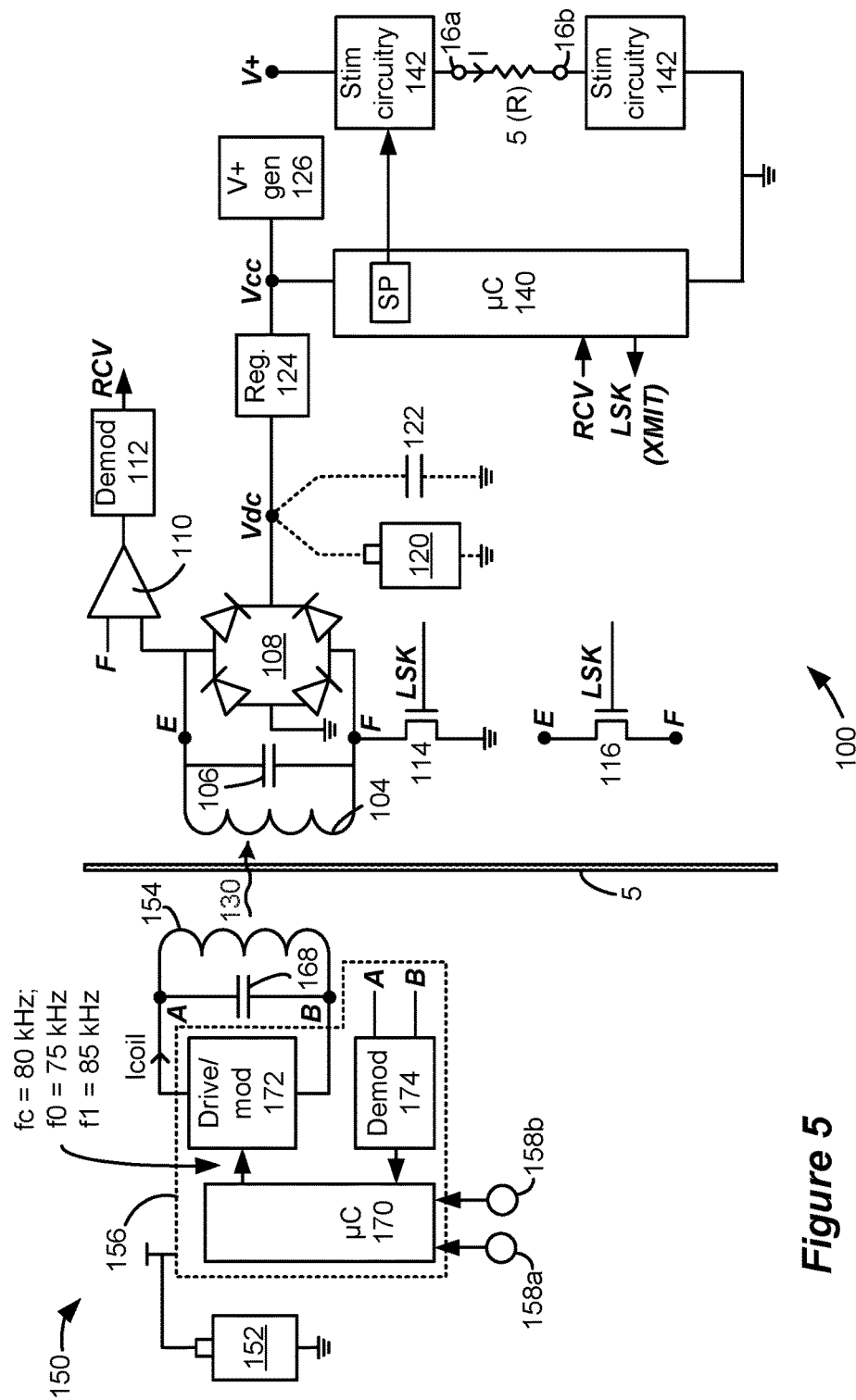
FIG. 5 shows circuitry useable in the charging patch and in the micro IPG, in accordance with an example of the invention.

Because the micro IPG 100 may lack an internal power source altogether, or may include only a small battery or capacitor, an external charging device such as a charging patch 150 is used to provide continuous power to the micro IPG 100. As shown in FIG. 4 and in the circuit diagram of FIG. 5, the patch 150 includes a battery 152 (preferably of a flat configuration, such as a coin-shaped battery), a primary charging coil 154 for producing a magnetic field 130, a capacitor 168 for tuning the frequency of the magnetic field in conjunction with an inductance of the coil 154, and various circuitry 156 shown in further detail in FIG. 5. Although the coil 154 and capacitor 168 are shown in FIG. 5 connected in parallel to create a resonant tank circuit, they may also be connected in series as is well known.

The magnetic field 130 produced by the patch 150 is preferably low enough in frequency that it is not significantly attenuated in the patient's tissue 5, and thus can comprise a frequency of 4 MHz or below. In one example, magnetic field 130 can comprise 80 kHz (fc). The magnetic field 130 is in turn received at a secondary coil 104 in the micro IPG 100. A capacitor 106 (FIG. 5) in the micro IPG 100 is used to set the resonant frequency of the IPG's tank circuit (104/106) to that of the magnetic field 130 for efficient reception. The received magnetic field 130 is rectified (108) and used to produce a DC voltage in the micro IPG 100, Vdc. Vdc can in one embodiment provide power to the remainder of the micro IPG 100's circuitry, and therefore require the patch 150 to be present and providing a magnetic field 130 for any aspect of the micro IPG 100 to operate. Alternatively, the micro IPG 100 can as shown in dotted lines in FIG. 5 include a small capacity power source, such as battery 120, or a capacitor 122 which can be charged to provide power for a small time (e.g., a few minutes). Having a small power source can be useful to attend to various housekeeping functions in the micro IPG 100, such as data storage, or possibly to allow communication with an external controller (e.g., 40 or 90, FIG. 2 or 3), which may for example be used to program the micro IPG 100 or set or adjust its stimulation program. If necessary, a regulator 124 can be included to smooth Vdc to a reliable voltage, Vcc, which can be used to power circuitry in the micro IPG 100, such as the microcontroller 140. Further, Vdc (or Vcc) can be boosted to a higher voltage by a generator 126, such as by boost circuitry that is used to produce a compliance voltage, V+, that powers the stimulation circuitry 142. Use of boost circuitry to generate V+ is discussed in U.S. Pat. No. 7,444,181 for example.

Preferably, the patch 150 can alter the strength of the magnetic field 130 it produces using telemetered feedback from the micro IPG 100. Thus, circuitry 156 includes a demodulator 174 for decoding data wirelessly received from the micro IPG 100; control circuitry (such as a microcontroller) 170 for interpreting such data; and drive and modulation circuitry 172. Drive and modulation circuitry 172 can set the strength of the AC current (Icoil) that will flow through the patch's coil 154 and hence the strength of the magnetic field 130 it produces. Data regarding how to set Icoil can come from telemetry circuitry in the micro IPG 100, which may transmit data to the patch 150 via Load Shift Keying (LSK) for example. As is known, LSK involves modulating the impedance of the coil 104 in the micro IPG 100 with data to be transmitted to the patch (e.g., Z), which causes decodable perturbations in the magnetic field 130 the patch 150 produces. Micro IPG 100 thus includes LSK circuitry for this purpose, represented as a transistor 116 capable of selectively shorting both ends of the coil 104 together in accordance with the data to be transmitted. LSK circuitry may also selectively short both ends of the coil 106 to ground, as represented by transistor 114. Telemetry of data from an implantable medical device to an external charger via LSK is discussed further in U.S. Patent Application Publication 2015/0080982. While magnetic field 130 adjustments are desirable, for example to ensure that Vdc is set to a proper level, it isn't strictly necessary that all embodiments of patch 150 have such capability, and instead continuous magnetic field 130 can be non-adjustable.

As discussed earlier, the patch 150 preferably also includes the ability to transmit data to the micro IPG 100 via drive and modulation circuitry 172. For example, at times when the patch 150 is used to change the stimulation program running in the micro IPG 100 (more on this below), data can be modulated on the magnetic field 130 using Frequency Shift Keying (FSK). In one example, the magnetic field 130 may be tuned to a center frequency (fc) of 80 kHz when not modulated with data and merely providing power, but may vary its frequency (e.g., f0=75 kHz; f1=85 kHz) when sending '0' and '1' data bits. Alternatively, data may be modulated on magnetic field 130 by various forms on amplitude or phase modulation. The micro IPG 100 may receive this data at an amplifier 110 connected to the receiving coil 104, which outputs the amplified data to demodulation circuitry 112, which in turn reports this data in digital form to a microcontroller 140 in the micro IPG 100. Such received data can include a stimulation program as discussed above, which informs stimulation circuitry 142 in the micro IPG 100 which electrodes 16 to stimulate and how to so stimulate them (e.g., frequency amplitude, duration, etc.). Stimulation circuitry 142 may be as described in U.S. Pat. Nos. 8,606,362 and 8,620,436 for example.

The patch 150 is preferably light weight may be disposable, and may generally resemble a band aid in structure. It is contemplated that the magnetic field 130 will be continuously produced until the battery 152 in the patch 150 is depleted, at which time a new patch 150 would need to be affixed to the patient. Alternatively, the battery 152 may be replaceable in the patch 150, thus allowing the patch to be re-used.

Referring again to FIG. 4, the housing 160 of the patch 150 may be made for example of a soft plastic material between which the coil 154 and other electronic components are sandwiched. If necessary, wings 162 outside of the area of the electronics may be included to promote affixation to the patient's skin above the implanted location of the micro IPG 100, and an adhesive 166 may be positioned under the wings 162. Alternatively, wings 162 may not be needed, and adhesive 166 can instead be placed underneath the electronics of the patch 150. While use of an adhesive 166 is preferred to affix the patch 150 at the location of the micro IPG 100, this is not strictly required and other means of positioning the patch 150 can be used as well. Although not shown, the patch 150 electronics can be supported within the housing 160 by a substrate, preferably a flexible substrate such as formed of Kapton for example. Further details concerning a charging patch such as 150 can be found in U.S. Provisional Patent Application Ser. No. 15/090,367, filed Apr. 4, 2016.

Due to its preferably simple construction, the patch 150 may contains no user interface elements. Alternatively, the patch may include simple means for adjusting the stimulation therapy being provided by the micro IPG 100. For example, the electronics of the patch 150 may include depressible bubble contacts 158a and 158b that are used to increase and decrease the amplitude of stimulation being provided by the stimulation program (SP) the micro IPG 100 is currently running. Notice that bubble contact 158a may be larger than bubble contact 158b, thus providing the patient easy means to feel which of the two contacts is to be used for increasing and decreasing stimulation. Alternatively, other devices may be used to provide power and also the data necessary to adjust stimulation therapy, such as the external controller 40 (FIG. 2) or clinician programmer 90 (FIG. 3) described earlier, thus leaving patch 150 to only provide operating power for the micro IPG 100. Such other means of communicating data to and from the micro IPG 100 may also occur at different frequencies than the continuously-provided magnetic field 130, thus allowing data communications to take place while the magnetic field 130 is present.

While a light weight patch 150 is preferred that can be fixed in position on the patient's skin relative to the micro IPG 100, micro IPG 100 can alternatively be powered by other external charging devices. For example, the micro IPG 100 may be powered by more traditional external charging devices, such as the external charger 50 described earlier (FIG. 2), even if the use of such bulkier devices, and/or devices which may move relative to the micro IPG 100, would be less convenient for the patient.

Figure 6:
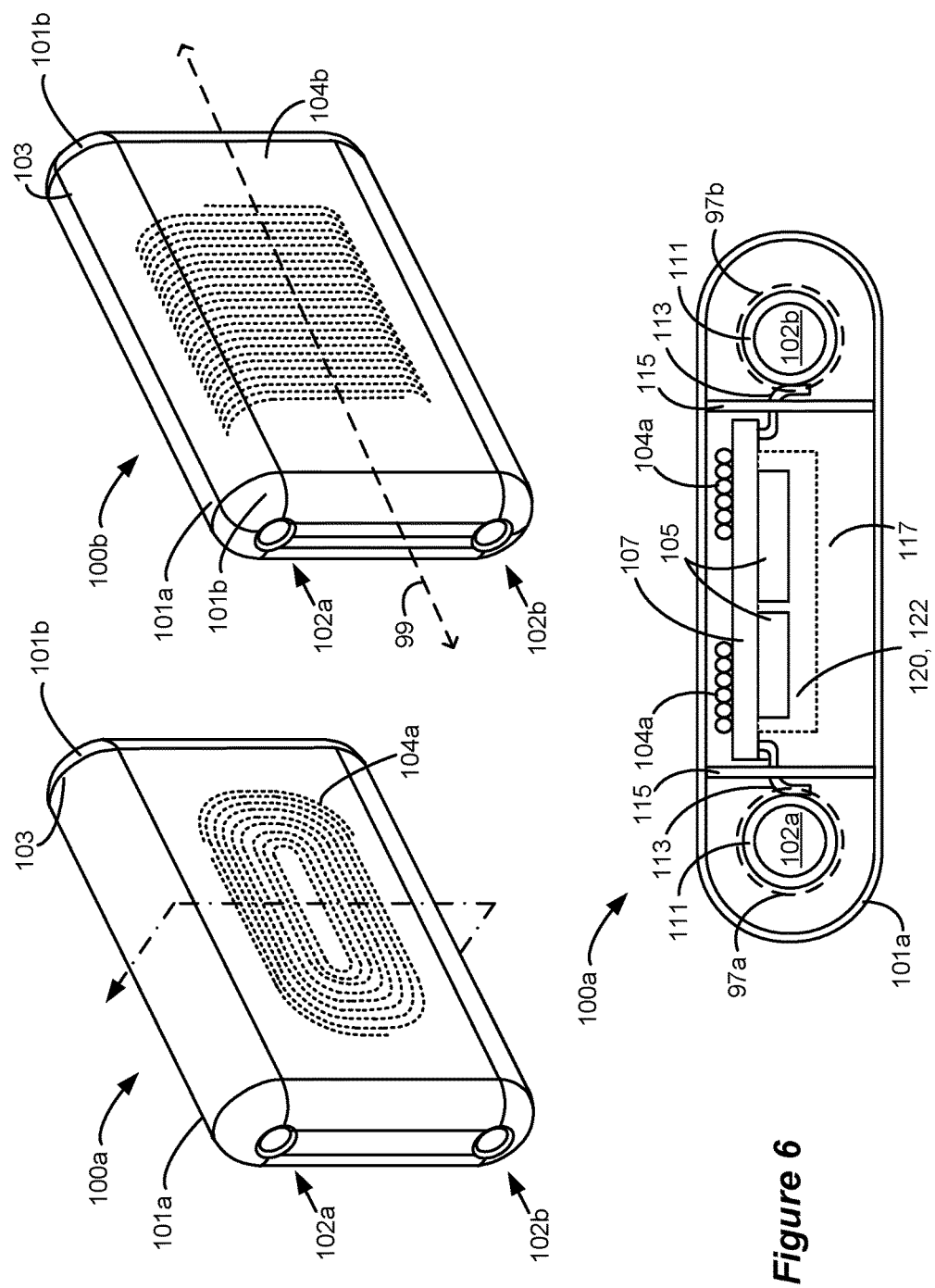
FIG. 6 shows a first example of a micro IPG, in accordance with an example of the invention.

FIG. 6 shows further details of the construction of the micro IPG 100 briefly shown earlier in FIG. 4. The top of FIG. 6 shows different examples 100a and 100b of the micro IPG having different configurations for its coil 104. In micro IPG 100a, the coil 104a is wound in a plane parallel with the plane of the coil 154 in the patch 150 when affixed to the patient's skin. In micro IPG 100b, the coil 104b is wound around an axis 99 that is parallel to the plane of the patch's coil 154. Coil 104a in micro IPG 100a would best couple with the coil 154, and thus most efficiently receive the magnetic field, but coil 104b in micro IPG 100b can also receive a sufficient amount of energy. As shown, the coils 104a and 104b in the micro IPG are within their housings 101a and 101b. If the housings 101a and 101b are formed of conductive materials, such as titanium, then they will attenuate the magnetic field 130 to some degree. To address this concern, housing 101a and 101b may also be formed of non-conductive materials, such as ceramic. If attenuation is a concern, coils 104a and 104b may also appear outside of the housings 101a and 101b, and connect to electronics in the housings via hermetic feedthroughs (not shown).

The bottom of FIG. 6 shows micro IPG 100a in cross section. Shown are the openings 102a and 102b, and one of the contacts 111 in the connector blocks 97a/b that contact one of the electrode terminals 20 at the proximal ends of the one of the leads 18. Each of the contacts 111 contacts a feedthrough pin 113, which pass though feedthroughs 115 that separate the openings 102a and 102b from a hermetic cavity 117 inside of the housing 101. Cavity 117 contains a printed circuit board (PCB) 107, including electronic components, such as are described in the micro IPG 100 with reference to FIG. 5. Additionally, PCB 107 may carry a small optional rechargeable battery 120 or storage capacitor 122 (FIG. 5) as mentioned previously. Also shown is coil 104, which in this example is within the housing 101, and more preferably within the cavity 117.

Also shown in FIG. 6 are various ways in which the housing 101 may be formed. At the top left of FIG. 6, housing 101 is divided into two sections 101a and 101b. Housing 101a comprises the majority of the housing, while housing 101b comprises an end portion formed on the opposite wall from the openings 102a and 102b. A weld or braze 103 is used to connect the housing 101a and 101b portions. At the top right of FIG. 6, housing portions 101a and 101b are shown as generally equal "clam shell" portions, affixed by a weld or braze 103.

While micro IPG 100 shows openings 102a/b and connector blocks 97a/b at opposite edges of the housing 101, the openings and connector blocks may also appear at different locations on the housing. For example, the openings/connector blocks may be stacked on top of one another in the z direction, or may even occur on opposite edges of the housing, although this isn't shown.

FIGS. 7A-7E show another example of a micro IPG 200 useable during a fully implantable trial stimulation period. Micro IPG 200 is similarly both in componentry and construction with IPGs disclosed in U.S. Provisional Patent Application entitled "Skull-Mounted Deep Brain Stimulator," Ser. No. 62/260,626 (the '626 Application), filed Nov. 29, 2015, which is incorporated herein by reference in its entirety.

Referring to FIG. 7A, micro IPG 200 is generally divided into three sections: an electronics section 210, a connector block section 230, and an electrode wire section 240. Sections 230 and 240 are further comprised in this example of left and right connector blocks 232a and 232b, each coupled to its own electrode wire cable 242a and 242b. In this example, each connector block 232/242 pair can couple to a proximal end (electrode terminals 20) of one of the eight-electrode leads 18 illustrated earlier (FIG. 1). However, the number of connector block/electrode wire cable pairs is application specific, and can comprise one or more than two. Micro IPG 200 is generally flexible at the electrode wire section 240. Unlike micro IPG 100, micro IPG 200's housing is generally cylindrical, and its connector blocks 232a/b are outside of and extend away from the housing.

As best seen in the cross section of FIG. 7B, electronics section 210 includes a cylindrically-shaped conductive housing 212 (shown underneath and in isolation in FIG. 7C), with a top cover 252 and a bottom cover 272 that are preferably laser welded to the housing 212. Housing 212 in this example also comprises a feedthrough 264 which is parallel to the top and bottom covers 252 and 272. However, it is not necessary that the housing 212 and feedthrough 264 be formed as one integral piece, and feedthrough 264 could for example be welded into place within the housing 212. The top cover 252 and feedthrough 264 generally define a hermetic cavity 301, while feedthrough 264, housing 212, and bottom cover 272 form a cavity 299 of superior hermeticity. Together, housing 212, top cover 252, and bottom cover 272 may be referred to as the "housing," and preferably comprise a conductive material such as titanium.

Figure 7D:
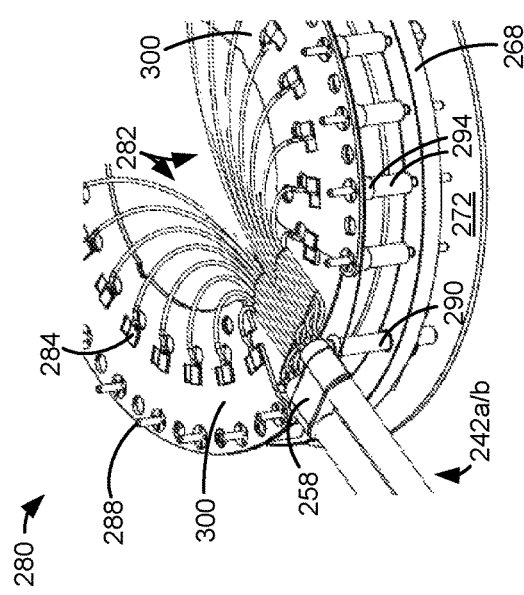
Figure 7C:
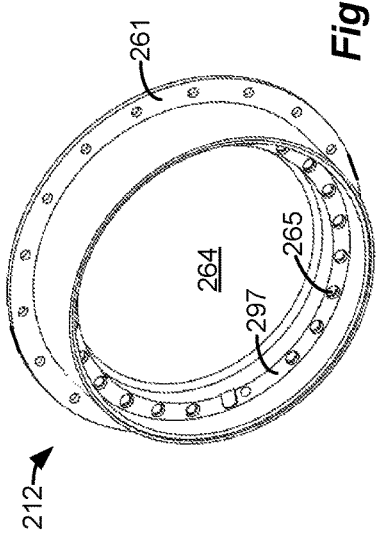

As seen best in FIGS. 7A and 7C, housing 212 is generally cylindrical. A silicone overmold 250 covers sharp edges of the housing 212 to provide soft surfaces for portions of the IPG 100 that might come into contact with a patient's tissue 5. Housing 212 includes a lip 261 with a hole (not shown) into which a leads retainer clip 258 (FIGS. 7A & 7D) can be pressed. Leads retainer clip 258 is ultimately held within the overmold 250 which also covers proximal ends of the electrode wire cables 242a/b. Top cover 252 includes a gap 253 (FIG. 7A) to allow the electrode wires cables 242a and 242b to enter cavity 301 in the housing 212. As will be explained further below, the housing is preferably grounded, and a hole 259 in the overmold 250 can serve to allow ground in the micro IPG 200 and the patient's tissue 5 to be tied together.

Housing 212 includes a charging coil 104, which as explained earlier is used to receive magnetic field 130 from the charging patch 150 to provide the micro IPG 200 continuous power. Alternatively, the IPG 100 may include a small rechargeable battery 120 or storage capacitor 122 to provide power to the micro IPG 200 (FIG. 5) for a short time, as discussed earlier. Electronics 105 in the micro IPG 200 are housed within cavity 299, and are integrated on a printed circuit board (PCB) 268. The underside of housing 212 includes a ledge 297 (FIGS. 7B & 7C) upon which the PCB 268 rests, although insulation may intervene between the two, as explained in the above-incorporated '626 Application. The feedthrough 264 includes holes 265 (FIGS. 7B & 7C), allowing feedthrough pins 288 to pass from cavity 301 to cavity 299, where they are connected to appropriate nodes on the PCB 268, again as explained in detail in the '626 Application. Coil 104 can appear in either cavity 301 or 299 of the housing, or even outside of the housing in other embodiments, as explained in the '626 Application.

Various electrical connections 280 are established inside cavity 301, as shown in FIG. 7D, which removes the housing 212 and top cover 252 for easier viewing. Electrode wires 282 from electrode wire cables 242a/b ultimately attach to various feedthrough pins 288, which connect to corresponding nodes on the PCB 268. Specifically, the electrode wires 282 from the electrode wire cables 242a/b (e.g., 8 wires in each) are connected to conductive terminals 284 formed in one or more substrates 300. The conductive terminals 284 may comprise crimps (tie bars) formed in conductive traces in the substrates 200, which are crimped (bent) over the ends of the wires 282. The substrate traces in turn lead to contacts that connect to the feedthrough pins 288. Further details concerning electrical connections 280 are explained in the '626 Application. Note that an insulator (not shown) can intervene between the electrical connections 280 and the feedthrough 264 to keep them from shorting. Also, ceramic beads and/or tubes 294 cab be sintered between the feedthrough pins 288 and the housing 212 to form a hermetic seal. Ground pins 290 couple the housing to ground on the PCB 268, as explained in the '626 Application.

Figure 7E:
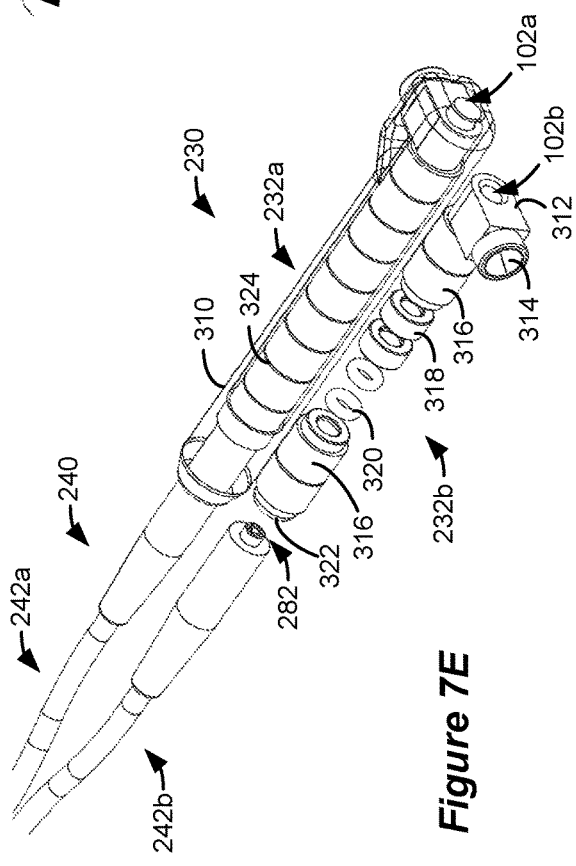

FIG. 7E shows further details of the connector block section 330, with some of the components of connector block 232b removed for easier viewing. Covering the components of the connector blocks 232a and 232b is an overmold 310, which may be made of silicone for example. The proximal ends of leads 18 with the electrode terminals 20 are inserted in openings 102a and 102b at locks 312 which can receive set screws (not shown) at perpendicular ports 314 to hold the leads 18 in place after they are fully inserted to end stops 322 in the connector blocks 232a and 232b. Each of the electrode terminals 20 when fully inserted will meet with a corresponding contact 320 formed of a deformable conductive material. Each contact 320 is encased in a conductive housing 318, and insulating seals 316 intervene between adjacent conductive housings 318 to keep them from shorting. Although not shown, electrode wires 282 from the electrode wire cables 242a and 242b proceed between the overmold 310 and the insulating seals 316, and each wire connects to a corresponding conductive housing 318/contact 320 at gaps 324 between the seals 316.

FIGS. 8A-8E show another example of a micro IPG 400 that can be used in the fully-implanted trial stimulation solution described above. Micro IPG 400 includes a rectangularly-shaped housing 402 explained in further detail with respect to FIG. 8D, with a feedthrough 412 allowing for the passage of feedthrough pins 414 therethrough. The feedthrough 414 pins connect with contacts 438 in two connector blocks 410a/b as explained in further detail with respect to FIG. 8B. The connector blocks 410a/b have openings 102a/b for the leads 18 as previously described. Unlike the micro IPG 100 described earlier (FIG. 4), the connector blocks 410a/b are stacked in the z direction. As a result, the z dimension of the micro IPG 400 is larger than micro IPG 100, but its Y dimension may be made shorter, especially if micro IPG 400 does not include a power source such as a battery 120 or storage capacitor 122 (FIG. 5).

Figure 8A:
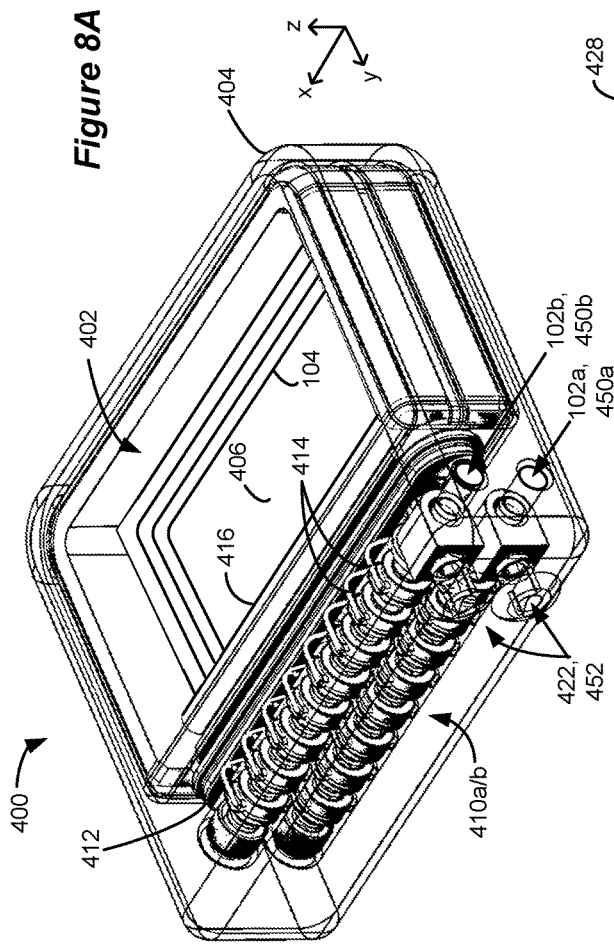

FIG. 8A shows micro IPG 400 with the top portion 402a (FIG. 8D) of the housing 402 removed so that internal structure can be seen. Housing 402 and feedthrough 412 define a hermetic cavity which houses a PCB 406 which carries the micro IPG electronics (FIG. 5) as well as its charging coil 104. Feedthrough pins 414 pass though the feedthrough 412 and are connected to nodes on a flexible connector 416 as best seen from the side view of FIG. 8E. Flexible connector 46 may comprise Kapton™ with electrical traces, which traces are then connected to the PCB 406 using standard means.

Figure 8B:
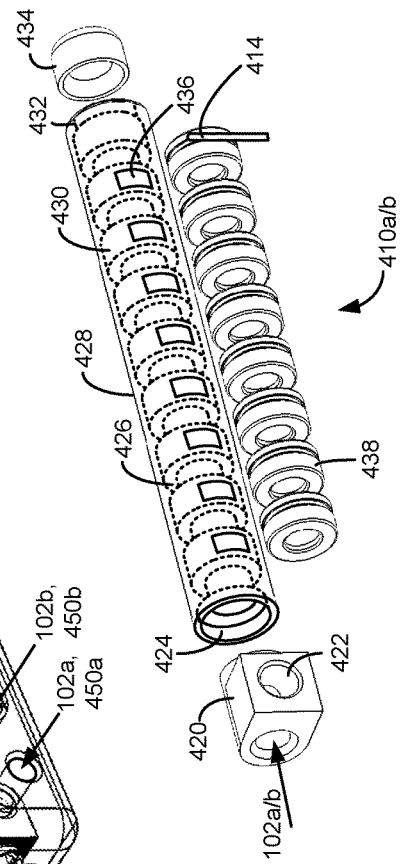

FIG. 8B shows further details of the connector blocks 410a/b, which may generally be constructed as separate assemblies as explained in U.S. Patent Application Publication 2015/0251011. Connector blocks 410 a/b also be used with the micro IPG 100 illustrated earlier.

Figure 1:
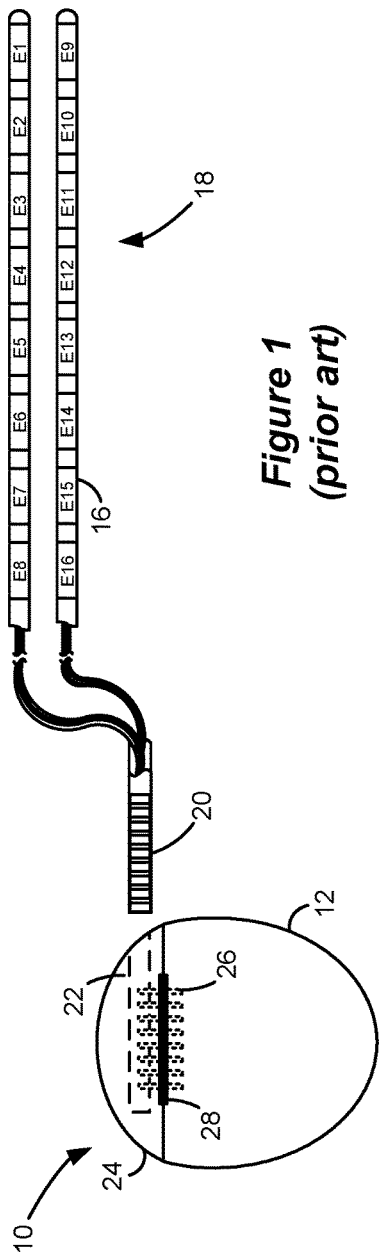
FIG. 1 shows an implantable pulse generator (IPG), in accordance with the prior art.

The connector blocks 410a/b are encased within an elastomer connector seal 428 formed of silicone for example, which has been molded to include contact recesses 430 separated by narrower-diameter separator portions 426 formed of the connector seal 428 material. The contact recesses 430 are accessible through slits 436 in the side of the connector seal 428. During construction, contacts 438, which are largely donut-shaped and formed of a rigid conductive material, are pressed through the slits 436, and come to rest inside of the seal 428 in the contact recesses 430. Once inserted, the header contacts 438 are captured firmly, and are electrically isolated from each other by the separator portions 426 of the connector seal 428. In the example shown, the connector seal 428 includes eight header contacts 438, which eventually will couple to the eight electrode terminals 20 at the proximal ends of one of the leads 18 (FIG. 1).

Once all header contacts 438 have been positioned in the seal 428, adhesive is applied to opening 424 at one end of the seal 428, and a lock 420 is inserted into the opening 424 and adhered to the connector seal 428. The lock 420 can receive a set screw (not shown) at perpendicular port 422. A platinum end cap 434 is also inserted into an opening 432 at the other end of the seal 428. Once the connector block subassemblies 410a/b are completed, they are mechanically and electrically connected to the feedthrough pins 414 emanating from the feedthrough 412. Specifically, ends of the feedthrough pins 414 are soldered to the header contacts 438 through the slits 436 in the connector seal 428.

The other end of the feedthrough pins 418 are connected to the fully fabricated PCB 406 (complete with the charging coil 104). Housing 402 is formed around the PCB 406 to form the hermetic cavity. First, the edges of the PCB 406 are made to rest on a ledge 440 of a plastic insert 403, as best shown in FIG. 8D. Insert 403 may be formed of Silopren™ LSR 7090 silicone rubber for example. Thereafter, top housing portion 402a and bottom housing portion 402b, both comprising a conductive material such as titanium for example, are formed around the insert 403 and an edge of the feedthrough 412. Edges 442 of the top and bottom housing portions 402a/b can be laser welded together, and edges 444 can be laser welded to the feedthrough 412.

Once the housing 402 has been so formed, a silicone overmold 404 may be formed around the housing 402 and the connector blocks 410a/b. The overmold 404 is shown in isolation in FIG. 8D, and includes openings 450 meeting with the openings 102a/b in the connector blocks 410a/b, and openings 452 for set screws (not shown) to be received at ports 422 on the locks 420. The overmold 404 may further include a hole 448 on either or both of its top and bottom to allow the grounded housing 402a/b to be tied to the patient's tissue 5. If it is desired that the top and bottom of micro IPG 400 be flat, a ground protrusion 446 can be formed in the housing portions 402a/b to match the thickness of the overmold 404 in these locations. Despite hole 448, silicone overmold 404 is generally formed over the connector blocks and over at least 50% of the top and bottom planar surfaces of the housing.

Each of the examples of micro IPGs have been shown as having two connector blocks, thus supporting two leads. However, this is not strictly necessary, and micro IPGs in other examples can include one or three or more connector blocks for receiving leads. "Housing" as used herein should be understood as separate and distinct from any overmolds that might cover the housing.

While the invention herein disclosed has been described by means of specific embodiments and applications thereof, numerous modifications and variations could be made thereto by those skilled in the art without departing from the scope of the invention set forth in the claims.

What is claimed is:

1. A system, comprising:
   an external charging device, wherein the external charging device comprises a primary charging coil configured to provide a magnetic field; and
   an implantable pulse generator, comprising
      a housing,
      electronic circuitry within the housing,
      a secondary charging coil configured to receive the magnetic field by magnetic induction to provide power to the electronic circuitry, at least one flexible electrode wire cable extending outwardly from the housing, wherein each flexible electrode wire cable comprises a plurality of electrode wires affixed to a substrate within the housing and in communication with the electronic circuitry; and a different connector block connected to each at least one flexible electrode wire cable outside of the housing, wherein each different connector block includes an opening into which a lead for stimulating a patient's tissue can be inserted and later removed, wherein the plurality of electrode wires in a flexible electrode wire cable connected to a connector block are connected to contacts in that connector block.

2. The system of claim 1, wherein the external charging device comprises a patch affixable to a skin of the patient proximate to the implantable pulse generator.

3. The system of claim 1, wherein the magnetic field provided by the external charging device is adjustable based on telemetered feedback from the implantable pulse generator.

4. The system of claim 1, wherein the secondary charging coil is within the housing.

5. The system of claim 1, wherein the secondary charging coil is outside of the housing.

6. The system of claim 1, wherein the housing is rectangular.

7. The system of claim 1, wherein the housing is cylindrical.

8. The system of claim 1, wherein the implantable pulse generator does not comprise a power source to provide power to the electronic circuitry.

9. The system of claim 1, wherein the implantable pulse generator comprises a power source, wherein the secondary charging coil is configured to provide power to the electronic circuitry by charging the power source configured to provide power to the electronic circuitry.

10. The system of claim 1, wherein the implantable pulse generator further comprises a silicone overmold encasing at least a portion of the housing.

11. The system of claim 1, wherein a frequency of the magnetic field is equal to or less than 4 MHz.

12. The system of claim 1, wherein the external charger is further configured to allow the patient to adjust a stimulation program being provided by the electronic circuitry by modulating data on the magnetic field.

13. The system of claim 1, wherein a volume of the implantable pulse generator is equal to or less than 5 cm$^3$.

14. An implantable pulse generator, comprising:

a housing;

electronic circuitry within the housing;

a secondary charging coil configured to receive a magnetic field by magnetic induction to provide power to the electronic circuitry;

at least one flexible electrode wire cable extending outwardly from the housing, wherein each flexible electrode wire cable comprises a plurality of electrode wires affixed to a substrate within the housing and in communication with the electronic circuitry; and a different connector block connected to each at least one flexible electrode wire cable outside of the housing, wherein each different connector block includes an opening into which a lead for stimulating a patient's tissue can be inserted and later removed, wherein the plurality of electrode wires in a flexible electrode wire cable connected to a connector block are connected to contacts in that connector block.

15. The implantable pulse generator of claim 14, wherein the implantable pulse generator does not comprise a power source to provide power to the electronic circuitry.

16. The implantable pulse generator of claim 14, wherein the implantable pulse generator comprises a power source, wherein the secondary charging coil is configured to provide power to the electronic circuitry by charging the power source configured to provide power to the electronic circuitry.

17. The implantable pulse generator of claim 14, wherein the housing is conductive or ceramic.

18. The implantable pulse generator of claim 14, wherein the secondary charging coil is within the housing.

19. The implantable pulse generator of claim 14, wherein the secondary charging coil is outside of the housing.

20. The implantable pulse generator of claim 14, wherein the implantable pulse generator further comprises a silicone overmold encasing at least a portion of the housing.

* * * * *